US011123365B2

(12) United States Patent
Perricone

(10) Patent No.: US 11,123,365 B2
(45) Date of Patent: Sep. 21, 2021

(54) COMPOSITIONS COMPRISING PALMITOYLETHANOLAMIDE AND HYDROGEN WATER, AND METHODS THEREOF

(71) Applicant: Perricone Hydrogen Water Company, LLC, Meriden, CT (US)

(72) Inventor: Nicholas V. Perricone, Madison, CT (US)

(73) Assignee: Perricone Hydrogen Water Company, LLC, Meriden, CT (US)

( * ) Notice: Subject to any disclaimer, the term of this patent is extended or adjusted under 35 U.S.C. 154(b) by 0 days.

(21) Appl. No.: 16/687,613

(22) Filed: Nov. 18, 2019

(65) Prior Publication Data

US 2021/0145864 A1 May 20, 2021

(51) Int. Cl.
| | | |
|---|---|---|
| *A61K 33/00* | (2006.01) | |
| *A61K 45/06* | (2006.01) | |
| *A61K 31/352* | (2006.01) | |
| *A61K 31/16* | (2006.01) | |

(52) U.S. Cl.
CPC .............. *A61K 33/00* (2013.01); *A61K 31/16* (2013.01); *A61K 31/352* (2013.01); *A61K 45/06* (2013.01)

(58) Field of Classification Search
CPC ...... A61K 33/00; A61K 31/16; A61K 31/352; A61K 45/06
USPC .......................................................... 424/600
See application file for complete search history.

(56) References Cited

U.S. PATENT DOCUMENTS

| | | | |
|---|---|---|---|
| 3,074,776 | A | 1/1963 | Ryan et al. |
| 3,425,859 | A | 2/1969 | Steigelman et al. |
| 3,655,448 | A | 4/1972 | Herbert |
| 3,963,460 | A | 6/1976 | Stumpf et al. |
| 4,337,295 | A | 6/1982 | Rittler et al. |
| 5,009,901 | A | 4/1991 | Byrne et al. |
| 5,382,714 | A | 1/1995 | Khachik |
| 5,648,564 | A | 7/1997 | Ausich et al. |
| 5,803,301 | A | 9/1998 | Sato et al. |
| 5,827,790 | A | 10/1998 | Evans et al. |
| 5,888,357 | A | 3/1999 | Mitsumori et al. |
| 6,017,599 | A | 1/2000 | Sakamoto et al. |
| 6,173,790 | B1 | 1/2001 | Russwurm et al. |
| 7,189,330 | B2 | 3/2007 | Hayashi et al. |
| 7,560,091 | B2 | 7/2009 | Hayashi et al. |
| 8,309,149 | B2 | 11/2012 | Yokoyama |
| 8,518,225 | B2 | 8/2013 | Sumita et al. |
| 8,574,503 | B2 | 11/2013 | Satoh et al. |
| 8,663,444 | B2 | 3/2014 | Nabeshima |
| 8,852,660 | B2 | 10/2014 | Miljkovic |
| 8,887,625 | B2 | 11/2014 | Satoh et al. |
| 8,974,646 | B2 | 3/2015 | Park et al. |
| 9,050,278 | B2 | 6/2015 | Ohta et al. |
| 9,120,672 | B2 | 9/2015 | Satoh et al. |
| 9,144,581 | B2 | 9/2015 | Miljkovic |
| 9,149,774 | B2 | 10/2015 | Satoh et al. |
| 9,511,331 | B2 | 12/2016 | Igarashi |
| 9,857,342 | B2 | 1/2018 | Tata |
| 10,076,540 | B1 | 9/2018 | Perricone |
| 10,155,010 | B1 | 12/2018 | Perricone |
| 2002/0162458 | A1 | 11/2002 | Farr et al. |

(Continued)

FOREIGN PATENT DOCUMENTS

| | | |
|---|---|---|
| CA | 2962376 A1 | 3/2016 |
| CN | 201347236 Y | 11/2009 |

(Continued)

OTHER PUBLICATIONS

Ishibashi et al. ("Consumption of water containing a high concentration of molecular hydrogen reduces oxidative stress and disease activity in patients with rheumatoid arthritis: an open-label pilot study" in Medical Gas Research, 2012, pp. 1-9, cited by applicant on form 1449).*
Impellizzen et al. ("Pamitoylethanolamide and luteolin ameliorate development of arthritis caused by injection of collagen type II in mice" in Arthritis Research & Therapy, 2013, 15:R192, pp. 1-14).*
Impellizzen et al. ("Micronized/ultramicronized palmitoylethanolamide displays superior oral efficacy compared to nonmicronized palmitoylethanolamide in a rat model of inflammatory pain" in Journal of Neuroinflammation 2014, 11:136, pp. 1-9).*
Russo et al. ("A tale of two cannabinoid: The therapeutic rationale for combining tetrahydrocannabinol and cannabidiol" in Medical Hypotheses (2006), No. 66, pp. 234-246).*
U.S. Appl. No. 15/834,262, filed Dec. 12, 2017, Perricone.

(Continued)

*Primary Examiner* — Blessing M Fubara
(74) *Attorney, Agent, or Firm* — Wolf, Greenfield & Sacks, P.C.

(57) ABSTRACT

Embodiments described herein generally relate to liquids, such as aqueous solutions, that contain hydrogen gas and palmitoylethanolamide. In certain cases, the liquids may also include active pharmaceutical agents (e.g., cannabinoids), noble gases, and/or other additives. Such liquids may be useful, for example, for increasing a subject's physical energy levels, for improvement in athletic performance, for the enhancement of the overall health of a subject, or the like. Some embodiments relate to liquids disposed within a container (e.g., a sealed container), such that the liquid comprises hydrogen gas and palmitoylethanolamide dissolved or otherwise contained (e.g., suspended and/or infused) in the liquid. The liquids (e.g., aqueous solutions) described herein may be orally administered to a subject (e.g., drunk by a subject). In certain embodiments, the hydrogen gas and/or palmitoylethanolamide may be present in the liquid at a particular concentration (e.g., a physiologically relevant concentration). Advantageously, the compositions, articles, and methods described herein provide liquids containing hydrogen gas and palmitoylethanolamide that are shelf-stable. For example, the liquid composition may maintain a relatively stable concentration of hydrogen gas and/or palmitoylethanolamide for relatively long periods of time (e.g., at least 7 days).

17 Claims, 1 Drawing Sheet

(56) References Cited

U.S. PATENT DOCUMENTS

| | | |
|---|---|---|
| 2005/0129621 A1 | 6/2005 | Davies et al. |
| 2005/0224996 A1 | 10/2005 | Yoshida |
| 2007/0017801 A1 | 1/2007 | Fukui et al. |
| 2007/0158449 A1 | 7/2007 | Hoffmann et al. |
| 2008/0311225 A1 | 12/2008 | Shiga |
| 2009/0035833 A1 | 2/2009 | Ohta et al. |
| 2010/0008849 A1 | 1/2010 | Martin |
| 2010/0008850 A1 | 1/2010 | Martin |
| 2010/0111830 A1 | 5/2010 | Boyden et al. |
| 2010/0163226 A1 | 7/2010 | Zornes |
| 2010/0233231 A1 | 9/2010 | Labrecque et al. |
| 2011/0111048 A1 | 5/2011 | Satoh et al. |
| 2011/0151058 A1 | 6/2011 | Yoshida |
| 2011/0155177 A1 | 6/2011 | Tamura et al. |
| 2011/0274922 A1 | 11/2011 | Yasue et al. |
| 2012/0070540 A1 | 3/2012 | Igarashi |
| 2012/0087990 A1 | 4/2012 | Shiga et al. |
| 2012/0107300 A1 | 5/2012 | Schirripa et al. |
| 2012/0289559 A1 | 11/2012 | Niwa et al. |
| 2013/0108515 A1 | 5/2013 | Satoh et al. |
| 2013/0122150 A1 | 5/2013 | Kim et al. |
| 2014/0010483 A1 | 1/2014 | Shih et al. |
| 2014/0027384 A1 | 1/2014 | Little et al. |
| 2014/0151321 A1 | 6/2014 | Chang et al. |
| 2014/0247689 A1 | 9/2014 | Wang et al. |
| 2014/0363361 A1 | 12/2014 | Wang et al. |
| 2015/0079197 A1 | 3/2015 | Kazama et al. |
| 2015/0104698 A1 | 4/2015 | Fung et al. |
| 2015/0121807 A1 | 5/2015 | Taber et al. |
| 2015/0197657 A1 | 7/2015 | Niederst et al. |
| 2015/0197863 A1 | 7/2015 | Kim et al. |
| 2015/0239760 A1 | 8/2015 | Kim et al. |
| 2015/0284280 A1 | 10/2015 | Huang et al. |
| 2016/0030387 A1 | 2/2016 | Winnicki et al. |
| 2016/0030470 A1 | 2/2016 | Huang et al. |
| 2016/0053596 A1 | 2/2016 | Rey |
| 2016/0054278 A1 | 2/2016 | Tata |
| 2016/0207765 A1 | 7/2016 | Takehara |
| 2016/0263535 A1 | 9/2016 | Lin |
| 2016/0353782 A1 | 12/2016 | Ruppman |
| 2017/0043932 A1 | 2/2017 | Byun et al. |
| 2017/0080022 A1 | 3/2017 | Levy |
| 2018/0338510 A1 | 11/2018 | Perricone |
| 2018/0338511 A1 | 11/2018 | Perricone |
| 2018/0338995 A1 | 11/2018 | Perricone |
| 2019/0046561 A1 | 2/2019 | Perricone |
| 2019/0046562 A1 | 2/2019 | Perricone |
| 2019/0046754 A1 | 2/2019 | Perricone |
| 2019/0046755 A1 | 2/2019 | Perricone |
| 2019/0047729 A1 | 2/2019 | Perricone |

FOREIGN PATENT DOCUMENTS

| | | |
|---|---|---|
| CN | 101961051 A | 2/2011 |
| CN | 105476480 A | 4/2016 |
| CN | 205312023 U | 6/2016 |
| CN | 106721799 A | 5/2017 |
| DE | 3048433 A1 | 7/1982 |
| EP | 767632 A1 | 4/1997 |
| EP | 2583937 A1 | 4/2013 |
| GB | 1014712 A | 12/1965 |
| GB | 2042398 A | 9/1980 |
| GB | 2496092 A | 5/2013 |
| JP | 8056632 | 3/1996 |
| JP | 2002301483 A | 10/2002 |
| JP | 2004351399 A | 12/2004 |
| JP | 3606466 B1 | 1/2005 |
| JP | 2007238100 A | 9/2007 |
| JP | 2008110342 A | 5/2008 |
| JP | 2008178769 A | 8/2008 |
| JP | 2008239598 A | 10/2008 |
| JP | 2008295436 A | 12/2008 |
| JP | 4383317 B2 | 12/2009 |
| JP | 4573904 B1 | 11/2010 |
| JP | 2013126650 A | 6/2013 |
| JP | 5699232 B1 | 4/2015 |
| JP | 5789907 B2 | 10/2015 |
| KR | 100678576 B1 | 10/2005 |
| KR | 20060035663 A | 4/2006 |
| KR | 20160124638 A | 10/2016 |
| RU | 95115488 A | 9/1997 |
| RU | 123685 U1 | 1/2013 |
| TW | 316922 B | 10/2005 |
| TW | 492296 U | 12/2014 |
| WO | WO 2002/002409 A1 | 1/2002 |
| WO | WO 2016146453 A1 * | 9/2006 |
| WO | WO 2008/029525 A1 | 3/2008 |
| WO | WO 2006/051588 A1 | 5/2008 |
| WO | WO 2008/072615 A1 | 6/2008 |
| WO | WO 2011/038799 A1 | 4/2011 |
| WO | WO 2012/073734 A1 | 6/2012 |
| WO | WO 2013/009928 A1 | 1/2013 |
| WO | WO 2014/145443 A2 | 9/2014 |
| WO | WO 2015/133409 A1 | 9/2015 |
| WO | WO 2015/175547 A1 | 11/2015 |
| WO | WO 2017/192755 A1 | 11/2017 |

OTHER PUBLICATIONS

U.S. Appl. No. 15/986,885, filed May 23, 2018, Perricone.

U.S. Appl. No. 15/671,403, filed Aug. 8, 2017, Perricone.

PCT/US2018/045538, Nov. 22, 2018, International Search Report and Written Opinion.

International Search Report and Written Opinion for Application No. PCT/US2018/045538 dated Nov. 22, 2018.

[No Author Listed], 500ml Drinking Hydrogen Rich Water Generator with built in lithium battery fastest delivery and shipping. Ali Express. Retrieved from https://www.aliexpress.com/item/500ml-Drinking-Hydrogen-Rich-Water-Generator-with-bulit-in-lithium-battery-fastest-delivery-and-shipping/32729940876.html?aff_platform=aaf&cpt=1484687007133&sk=JEYRB2F&aff_trace_ key=bc5bdfad4e864ea2910a88ec8daf3271-1484687007133-06041-JEYRB2F. Date accessed: Oct. 25, 2017. 3 pages.

[No Author Listed], Applications Vacuum Barrier Corporation. Retrieved from http://vacuumbarrier.com/applications/. Last Accessed: Mar. 6, 2017. 1 page.

[No Author Listed], Blue Mercury Product Information. Retrieved from http://www.bluemercury.co.jp/e/product_introduction.html. Date accessed: Oct. 25, 2017. 1 page.

[No Author Listed], H2 Hydrogen Water Pack. Retrieved from http://www.hydrogenwater-stick.com/. Date accessed: Oct. 25, 2017. 6 pages.

[No Author Listed], Liquid Nitrogen Dosing System: Standard Features. Inline Filling Systems. Retrieved from http://www.fillers.com/liquid-nitrogen-dosing-system/. Date accessed: Mar. 6, 2017. 2 pages.

[No Author Listed], What happens if you mix water with liquid hydrogen? Quora. Retrieved from https://www.quora.com/What-happens-if-you-mix-water-with-liquid-hydrogen. Date accessed: Oct. 25, 2017. 2 pages.

[No Author Listed], Alchemia Nova "Noble Gas Waters," pp. 1-3. http://www.alchemianova.com/articles/nobles.ntml, 20005. (Year: 2001).

[No Author Listed], Brown's Gas, How Much PPM of hydrogen will the Aquacure infuse into water? http://www.eagle-research.com/cms/faq/brown-gas/brown-gas-healthenhancement. (Year: 2005).

[No Author Listed], Valspar Packaging. Aug. 3, 2016. Retrieved from https://www.youtube.com/watch?v=lzSxyJzMK34.

[No Author Listed], INERIS, Jun. 2017. Retrieved from https://substitution.ineris.fr/sites/substitution-portail/files/newsletter_sna_11_en_0.pdf.

Cleveland et al., Continuously Infusing Hyperpolarized 129Xe into Flowing Aqueous Solutions Using Hydrophobic Gas Exchange Membranes. J Phys Chem B. Sep. 17, 2009; 113(37): 12489-12499.

Esencan et al., XENON in medical area: emphasis on neuroprotection in hypoxia and anesthesia. Med Gas Res. Feb. 1, 2013;3(1):4. doi: 10.1186/2045-9912-3-4.

(56) References Cited

OTHER PUBLICATIONS

Geueke, Dossier—Can Coatings. Dec. 2016. Retrieved from https://www.foodpackagingforum.org/fpf-2016/wp-content/uploads/2016/FPF_Dossier11_cancoatings-1.pdf.
Gharib et al., Anti-inflammatory properties of molecular hydrogen: investigation on parasite-induced liver inflammation. C R Acad Sci III. Aug. 2001;324(8):719-24.
Harris et al., Neuroprotection against traumatic brain injury by xenon, but not argon, is mediated by inhibition at the N-methyl-D-aspartate receptor glycine site. Anesthesiology. Nov. 2013;119(5):1137-48. doi: 10.1097/ALN.0b013e3182a2a265.
Harris, Measuring out fluids microdrop by microdrop. Machine Design. Dec. 7, 2000. 8 pages.
Hiraoka et al., Studies on the properties and real existence of aqueous solution systems that are assumed to have antioxidant activities by the action of "active hydrogen." Journal of Health Sciences. 2004; 50(5):456-465.
Ishibashi et al., Consumption of water containing a high concentration of molecular hydrogen reduces oxidative stress and disease activity in patients with rheumatoid arthritis: an open-label pilot study. Med Gas Res. Oct. 2, 2012;2(1):27. doi: 10.1186/2045-9912-2-27.
Kang et al., Effects of drinking hydrogen-rich water on the quality of life of patients treated with radiotherapy for liver tumors. Med Gas Res. Jun. 7, 2011;1(1):11. doi: 10.1186/2045-9912-1-11.
Koh et al., Xenon gas as a performance-enhancing drug: doping or just hot air? Cycling Tips. Retrieved from https://cyclingtips.com/2014/03/xenon-gas-as-a-performance-enhancing-drug-doping-or-just-hot-air/. Date accessed: Oct. 25, 2017. 11 pages.
Kurita et al., Measurements of hydrogen permeation through fused silica and borosilicate glass by electrochemical pumping using oxide protonic conductor. Solic State Ionics. 2002;146:101-11.
Nicolson et al., Clinical Effects of Hydrogen Administration: From Animal and Human Diseases to Exercise Medicine. International Journal of Clinical Medicine. Jan. 2016;7(1):32-76.
Shen et al., A review of experimental studies of hydrogen as a new therapeutic agent in emergency and critical care medicine. Med Gas Res. Nov. 8, 2014;4:17. doi: 10.1186/2045-9912-4-17. eCollection 2014.
Soto et al., Evidence of Absence: Estrogenicity Assessment of a New Food-Contact Coating and the Bisphenol Used in Its Synthesis. Environ Sci Technol. Feb. 7, 2017;51(3):1718-1726. doi: 10.1021/acs.est.6b04704. Epub Jan. 18, 2017.
Taleyarkhan, Modeling & Analysis of Liquid Deuterium-Water Reactions. Oak Ridge National Laboratory. 1995. 10 pages.
Verkhovskaya et al., Manufacturing the Technology of Xenon Containing Drinking Water and its Influence on Some Psychophysiological Characteristics of Man. Publicly disclosed on May 25-28, 2016.
International Preliminary Report on Patentability for Application No. PCT/US2018/045538 dated Feb. 20, 2020.
[No Author Listed], Hydrogen—Thermophysical Properties. The Engineering ToolBox. 2008. Retrieved from https://www.engineeringtoolbox.com/hydrogen-d_1419.html. Accessed Feb. 21, 2021. 3 pages.
[No Author Listed], Argon—Thermophysical Properties. The Engineering ToolBox. 2008. Retrieved from https://www.engineeringtoolbox.com/argon-d_1414.html. Accessed Feb. 21, 2021. 2 pages.
[No Author Listed], Critical Points for some Substances. The Engineering ToolBox. 2005. Retrieved from https://www.engineeringtoolbox.com/critical-point-d_997.html. Accessed Feb. 21, 2021. 2 pages.
[No Author Listed], Proximate. Lexico. Definition, Retrieved from https://www.lexico.com/en/definition/proximate. Accessed Feb. 21, 2021. 1 page.
Arrieta et al., Hazards of Inert Gases and Oxygen Depletion. EIGA. 2009. Retrieved from https://www.linde-gas.com/en/images/Hazards%20of%20inert%20gases%20and%20oxygen%20depletion_tcm17-13909.pdf Accessed Apr. 21, 2021. 24 pages.
U.S. Appl. No. 15/671,391, filed Aug. 8, 2017, Perricone.
U.S. Appl. No. 15/671,465, filed Aug. 8, 2017, Perricone.
PCT/US2018/045538, Feb. 20, 2020, International Preliminary Report on Patentability.

\* cited by examiner

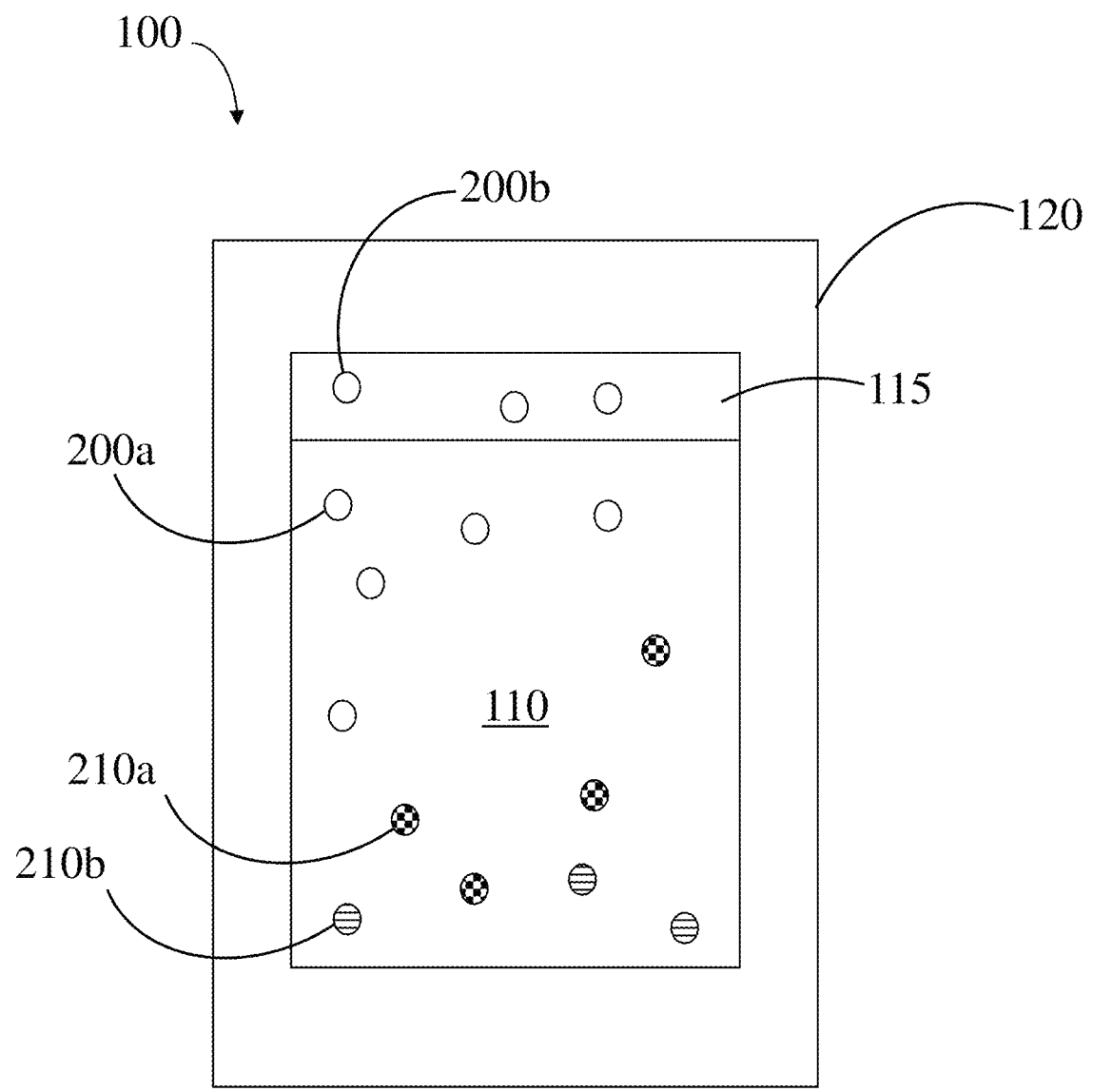

COMPOSITIONS COMPRISING PALMITOYLETHANOLAMIDE AND HYDROGEN WATER, AND METHODS THEREOF

FIELD

Compositions, articles, and methods generally related to liquids containing hydrogen and palmitoylethanolamide are described herein.

BACKGROUND

Hydrogen has been shown to have positive effects on animal and human physiology and disease states. Hydrogen can be administered to a subject in the form of, for example, a gas, an infusion, a topical solution, or through the drinking of hydrogen-enriched water. Production of hydrogen-enriched water has been accomplished by several methods, ranging from large-scale, but less self-stable, manufacturing techniques to small-volume single use devices for locally generating hydrogen gas.

SUMMARY

Compositions, articles, and methods generally related to liquids containing hydrogen and palmitoylethanolamide are described herein. The subject matter of the present invention involves, in some cases, interrelated products, alternative solutions to a particular problem, and/or a plurality of different uses.

Some aspects are generally directed to articles. In one set of embodiments, the article comprises an aqueous solution contained within a container. In some cases, the aqueous solution comprises palmitoylethanolamide and dissolved hydrogen gas at a concentration greater than 1 ppm.

Certain aspects are generally directed to methods. In one set of embodiments, the method comprises drinking an aqueous solution, where the aqueous solution comprises dissolved hydrogen gas at a concentration greater than 1 ppm, and dissolved and/or suspended palmitoylethanolamide. In another set of embodiments, the method comprises administering an aqueous solution to a subject, where the aqueous solution comprises dissolved hydrogen gas at a concentration greater than 1 ppm, and dissolved and/or suspended palmitoylethanolamide.

The method, in yet another set of embodiments, comprises providing a container comprising water, dissolving hydrogen in the water such that the water comprises hydrogen gas at a concentration greater than or equal to 1 ppm, and dissolving and/or suspending palmitoylethanolamide in the water. In some cases, the palmitoylethanolamide is dissolved in the water using an emulsifier and/or suspended in the water using micronization.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

The FIGURE is, according to certain embodiments, a schematic drawing illustrating an article comprising an aqueous solution disposed within a container.

Other aspects, embodiments and features will become apparent from the following detailed description when considered in conjunction with the accompanying drawings. The accompanying figures are schematic and are not intended to be drawn to scale. For purposes of clarity, not every component is labeled in every FIGURE, nor is every component of each embodiment shown where illustration is not necessary to allow those of ordinary skill in the art to understand the description herein. All patent applications and patents incorporated herein by reference are incorporated by reference in their entirety. In case of conflict, the present specification, including definitions, will control.

DETAILED DESCRIPTION

Embodiments described herein generally relate to liquids, such as aqueous solutions, that contain hydrogen gas and palmitoylethanolamide. In certain cases, the liquids may also include active pharmaceutical agents (e.g., cannabinoids), noble gases, and/or other additives. Such liquids may be useful, for example, for increasing a subject's physical energy levels, for improvement in athletic performance, for the enhancement of the overall health of a subject, or the like. Some embodiments relate to liquids disposed within a container (e.g., a sealed container), such that the liquid comprises hydrogen gas and palmitoylethanolamide dissolved or otherwise contained (e.g., suspended and/or infused) in the liquid. The liquids (e.g., aqueous solutions) described herein may be orally administered to a subject (e.g., drunk by a subject). In certain embodiments, the hydrogen gas and/or palmitoylethanolamide may be present in the liquid at a particular concentration (e.g., a physiologically relevant concentration). Advantageously, the compositions, articles, and methods described herein provide liquids containing hydrogen gas and palmitoylethanolamide that are shelf-stable. For example, the liquid composition may maintain a relatively stable concentration of hydrogen gas and/or palmitoylethanolamide for relatively long periods of time (e.g., at least 7 days).

In one aspect, generally, the article comprises a liquid comprising hydrogen gas ($H_2$) and palmitoylethanolamide. In some embodiments, the liquid is an aqueous solution. For example, in some cases, the liquid is water, optionally with any number of a variety of additives, such as sugar, electrolytes, caffeine, salt, flavoring, vitamins, herbs, amino acids, tea extracts, seed extracts, fruit extracts. The liquid (e.g., aqueous solution) may in some cases be any of a variety of drinkable liquids, such as a fruit juice, coffee, tea, a sports drink, an energy drink, soda pop, milk, an alcoholic drink, or the like. In certain embodiments, the liquid (e.g., aqueous solution) may be configured to be administered (e.g., orally, intravenously, etc.) to a subject. For example, the liquid (e.g., aqueous solution) may be in the form of a drink (e.g., a sports drink, an energy drink, etc.) or an intravenous fluid (e.g., saline).

In certain aspects, the composition, article, and/or liquid (e.g., aqueous solution) comprises hydrogen. Without wishing to be bound by theory, hydrogen may act within the body as an antioxidant. In some cases, hydrogen may be used to treat various oxidative stress conditions, for example, as an antioxidant, or by interaction with proteins such as nuclear factor erythroid 2-related factor 2 (NRF2). For example, strenuous exercise may cause oxidative stresses (e.g., due to muscle fatigue). Hydrogen may accordingly be used in some embodiments to treat athletes and improve athletic performance. Thus, in some cases, compositions such as those discussed herein (e.g., containing hydrogen gas) may be provided to a subject to enhance athletic performance.

In addition, in some cases, hydrogen may be used to treat oxidative stress diseases and conditions such as smoking, exposure to ultraviolet rays, air pollution, aging, physical or psychological stress, cancer, or the aging process. Hydrogen may also exhibit other effects, such as anti-inflammatory properties, that may be useful in conjunction with palmitoylethanolamide, which is explained herein in greater detail.

In certain aspects, hydrogen is dissolved in the liquid (e.g., aqueous solution). Methods of dissolving hydrogen in the liquid are explained herein in greater detail. The FIGURE is, according to certain embodiments, a schematic drawing illustrating an article comprising an aqueous solution contained within a container. Referring to the FIGURE, article 100 comprises container 120 comprising liquid (e.g., aqueous solution) 110. In certain embodiments, liquid 110 comprises dissolved hydrogen gas 200a. In some aspects, in addition to being dissolved in the liquid, the hydrogen gas is also present in the headspace of the container, which is described herein in greater detail.

In certain embodiments, the particular amount of hydrogen gas present in the liquid is an amount that would have an effect (e.g., physiological effect) in and/or on the body of a subject. Accordingly, the liquid may comprise hydrogen gas in any of a variety of suitable amounts. For example, in some embodiments, the liquid (e.g., aqueous solution) comprises the hydrogen gas at a concentration greater than or equal to 0.1 ppm, greater than or equal to 0.2 ppm, greater than or equal to 0.3 ppm, greater than or equal to 0.4 ppm, greater than or equal to 0.5 ppm, greater than or equal to 0.6 ppm, greater than or equal to 0.7 ppm, greater than or equal to 0.8 ppm, greater than or equal to 0.9 ppm, greater than or equal to 1 ppm, greater than or equal to 1.1 ppm, greater than or equal to 1.2 ppm, greater than or equal to 1.25 ppm, greater than or equal to 1.3 ppm, greater than or equal to 1.4 ppm, greater than or equal to 1.5 ppm, greater than or equal to 1.6 ppm, greater than or equal to 1.7 ppm, greater than or equal to 1.75 ppm, greater than or equal to 1.8 ppm, greater than or equal to 1.9 ppm, greater than or equal to 2 ppm, greater than or equal to 2.25 ppm, greater than or equal to 2.5 ppm, greater than or equal to 2.75 ppm, greater than or equal to 3 ppm, greater than or equal to 3.25 ppm, greater than or equal to 3.5 ppm, greater than or equal to 3.75 ppm, greater than or equal to 4 ppm, greater than or equal to 4.25 ppm, greater than or equal to 4.5 ppm, or greater than or equal to 4.75 ppm.

In certain embodiments, the liquid comprises hydrogen gas at a concentration less than or equal to 5 ppm, less than or equal to 4.75 ppm, less than or equal to 4.5 ppm, less than or equal to 4.25 ppm, less than or equal to 4 ppm, less than or equal to 3.75 ppm, less than or equal to 3.5 ppm, less than or equal to 3.25 ppm, less than or equal to 3 ppm, less than or equal to 2.75 ppm, less than or equal to 2.5 ppm, less than or equal to 2.25 ppm, less than or equal to 2 ppm, less than or equal to 1.9 ppm, less than or equal to 1.8 ppm, less than or equal to 1.75 ppm, less than or equal to 1.7 ppm, less than or equal to 1.6 ppm, less than or equal to 1.5 ppm, less than or equal to 1.4 ppm, less than or equal to 1.3 ppm, less than or equal to 1.25 ppm, less than or equal to 1.2 ppm, less than or equal to 1.1 ppm, less than or equal to 1 ppm, less than or equal to 0.9 ppm, less than or equal to 0.8 ppm, less than or equal to 0.7 ppm, less than or equal to 0.6 ppm, less than or equal to 0.5 ppm, less than or equal to 0.4 ppm, less than or equal to 0.3 ppm, or less than or equal to 0.2 ppm. Combinations of the above-referenced ranges are also possible (e.g., the liquid comprises the hydrogen gas at a concentration greater than or equal to 0.1 ppm and less than or equal to 5 ppm, the liquid comprises the hydrogen gas at a concentration greater than or equal to 1.5 ppm and less than or equal to 2 ppm). Other ranges are also possible.

In certain aspects, the composition, article, and/or liquid (e.g., aqueous solution) comprises palmitoylethanolamide. According to some embodiments, palmitoylethanolamide may bind to receptors in the cell-nucleus to relieve chronic pain and inflammation. Without wishing to be bound by theory, palmitoylethanolamide may bind to peroxisome proliferator-activated receptor alpha (PPAR-alpha) and/or cannabinoid-like G-coupled receptors such as GPR55 and GPR119. According to some aspects, palmitoylethanolamide may have anti-inflammatory, anti-nociceptive, neuroprotective, cardioprotective, and/or anticonvulsant properties.

In certain embodiments, at least a portion of the palmitoylethanolamide is dissolved in the liquid (e.g., aqueous solution). For example, referring to the FIGURE, liquid 110 comprises dissolved palmitoylethanolamide 210. Without wishing to be bound by theory, palmitoylethanolamide has low solubility in water (e.g., less than 20 mM). Accordingly, in certain embodiments, the palmitoylethanolamide may be dissolved in the liquid (e.g., aqueous solution) using an emulsifier. In some aspects, palmitoylethanolamide may be dissolved in the liquid (e.g., aqueous solution) to levels of saturation.

Methods other than dissolving palmitoylethanolamide in the liquid (e.g., water) may be necessary to prepare the articles described herein in some embodiments. According to some aspects, for example, at least a portion of the palmitoylethanolamide is suspended in the liquid (e.g., aqueous solution). As shown in the FIGURE, for example, liquid 110 comprises suspended palmitoylethanolamide 210b. In some aspects, the suspended palmitoylethanolamide may be micronized. As used herein, the term "micronized" or "micronization" refers the process of reducing the average diameter of a solid particle to the micrometer, and in some cases, the nanometer range. Advantageously, the micronization of the palmitoylethanolamide may facilitate the administration of the composition to a subject and/or increase the efficacy of the palmitoylethanolamide, in certain embodiments. Without wishing to be bound by theory, the solubility of palmitoylethanolamide in water is low, therefore requiring the palmitoylethanolamide in the composition to be prepared for administration to the subject via methods other than just dissolving the palmitoylethanolamide in the liquid (e.g., aqueous solution) to levels of saturation, as explained above. Accordingly, the palmitoylethanolamide may be micronized into particles small enough to be easily consumed and/or digested by the subject upon consumption of the liquid, at least in certain embodiments. In addition, micronization of the palmitoylethanolamide into micronized particles may increase the surface area of the palmitoylethanolamide, such that when the palmitoylethanolamide is administered and/or consumed by the subject, the effects of palmitoylethanolamide may be realized at a faster rate as compared to a composition that did not have micronized palmitoylethanolamide but is otherwise equivalent. Methods of micronization would be understood to one or ordinary skill in the art, including milling (e.g., ball milling), grinding, bashing, and/or pulverizing the palmitoylethanolamide. In certain embodiments, supercritical fluids may be used in the micronization process, using, for example, supercritical anti-solvents to precipitate micronized particles from solution. Without wishing to be bound by theory, the micronization of palmitoylethanolamide may also facilitate the dissolution of the palmitoylethanolamide in the liquid (e.g., aqueous solution).

In certain non-limiting embodiments, at least a portion of the palmitoylethanolamide may be dissolved in the liquid (e.g., aqueous solution) and at least a portion of the palmitoylethanolamide may be suspended in the liquid (e.g., aqueous solution).

In some cases, palmitoylethanolamide may exhibit synergistic effects with hydrogen gas and/or other components of the compositions described herein (e.g., active pharmaceutical agents, such as cannabinoids). For example, palmitoylethanolamide and hydrogen gas may exhibit synergistic effects for certain applications such as for the treatment of animal and human diseases, for improvement in athletic performance, for the enhancement of the overall health of a subject, or the like. In certain embodiments, palmitoylethanolamide and hydrogen gas may synergistically provide anti-inflammatory effects to a subject. In addition, palmitoylethanolamide and hydrogen gas may synergistically relieve symptoms and/or treat a subject with arthritis and/or rheumatoid arthritis.

Advantageously, the synergistic effects exhibited by palmitoylethanolamide and hydrogen gas may be greater than each of the individual effects of palmitoylethanolamide and hydrogen gas. In some cases, the synergistic effects exhibited by palmitoylethanolamide and hydrogen gas may be greater than the sum of their individual effects. Accordingly, the articles described herein are more effective at treating a subject than conventional sources of hydrogen gas or palmitoylethanolamide (e.g., a supplement and/or capsule of palmitoylethanolamide). Without wishing to be bound by theory, such synergistic effects are realized by effectively dissolving palmitoylethanolamide in the aqueous solution (e.g., using an emulsifier) and/or suspending palmitoylethanolamide in the aqueous solution (e.g., using micronization) in the presence of hydrogen gas.

According to certain embodiments, palmitoylethanolamide is micronized such that the suspended palmitoylethanolamide comprises a plurality of particles (e.g., microparticles, nanoparticles). In certain embodiments, the particles may have any of a variety of suitable average particle sizes (e.g., average particle diameters). For example, in certain aspects, the palmitoylethanolamide comprises a plurality of particles having an average particle size of less than or equal to 1000 micrometers, less than or equal to 750 micrometers, less than or equal to 500 micrometers, less than or equal to 250 micrometers, less than or equal to 1 micrometer, less than or equal to 750 nm, less than or equal to 500 nm, less than or equal to 250 nm, less than or equal to 100 nm, or less than or equal to 50 nm. In certain embodiments, the palmitoylethanolamide comprises a plurality of particles having an average particle size of greater than or equal to 1 nm, greater than or equal to 50 nm, greater than or equal to 100 nm, greater than or equal to 250 nm, greater than or equal to 500 nm, greater than or equal to 750 nm, greater than or equal to 1 micrometer, greater than or equal to 250 micrometers, greater than or equal to 500 micrometers, or greater than or equal to 750 micrometers. Combinations of the above-referenced ranges are also possible (e.g., the palmitoylethanolamide comprises a plurality of particles having an average particle size of less than or equal to 1000 micrometers and greater than or equal to 1 nm, the palmitoylethanolamide comprises a plurality of particles having an average particle size of less than or equal to 250 micrometers and greater than or equal to 500 nm). Other ranges are also possible.

The particular amount of palmitoylethanolamide present in the liquid (e.g., dissolved and/or suspended) is an amount that would have an effect (e.g., physiological effect) in and/or on the body of a subject. Accordingly, the liquid may comprise palmitoylethanolamide in any of a variety of suitable amounts. For example, in some embodiments, the liquid (e.g., aqueous solution) comprises dissolved palmitoylethanolamide at a concentration greater than or equal to 1 ppm, greater than or equal to 1.25 ppm, greater than or equal to 1.5 ppm, greater than or equal to 1.75 ppm, greater than or equal to 2 ppm, greater than or equal to 2.25 ppm, greater than or equal to 2.5 ppm, greater than or equal to 2.75 ppm, greater than or equal to 3 ppm, greater than or equal to 3.25 ppm, greater than or equal to 3.5 ppm, greater than or equal to 3.75 ppm, greater than or equal to 4 ppm, greater than or equal to 4.25 ppm, greater than or equal to 4.5 ppm, greater than or equal to 4.75 ppm, greater than or equal to 5 ppm, greater than or equal to 5.5 ppm, greater than or equal to 6 ppm, greater than or equal to 6.5 ppm, greater than or equal to 7 ppm, greater than or equal to 7.5 ppm, greater than or equal to 8 ppm, greater than or equal to 8.5 ppm, greater than or equal to 9 ppm, greater than or equal to 9.5 ppm, greater than or equal to 10 ppm, greater than or equal to 11 ppm, greater than or equal to 12 ppm, greater than or equal to 13 ppm, greater than or equal to 14 ppm, greater than or equal to 15 ppm, greater than or equal to 16 ppm, greater than or equal to 17 ppm, greater than or equal to 18 ppm, or greater than or equal to 19 ppm.

In certain embodiments, the liquid (e.g., aqueous solution) comprises dissolved palmitoylethanolamide at a concentration less than or equal to 20 ppm, less than or equal to 19 ppm, less than or equal to 18 ppm, less than or equal to 17 ppm, less than or equal to 16 ppm, less than or equal to 15 ppm, less than or equal to 14 ppm, less than or equal to 13 ppm, less than or equal to 12 ppm, less than or equal to 11 ppm, less than or equal to 10 ppm, less than or equal to 9.5 ppm, less than or equal to 9 ppm, less than or equal to 8.5 ppm, less than or equal to 8 ppm, less than or equal to 7.5 ppm, less than or equal to 7 ppm, less than or equal to 6.5 ppm, less than or equal to 5 ppm, less than or equal to 4.75 ppm, less than or equal to 4.5 ppm, less than or equal to 4.25 ppm, less than or equal to 4 ppm, less than or equal to 3.75 ppm, less than or equal to 3.5 ppm, less than or equal to 3.25 ppm, less than or equal to 3 ppm, less than or equal to 2.75 ppm, less than or equal to 2.5 ppm, less than or equal to 2.25 ppm, less than or equal to 2 ppm, less than or equal to 1.75 ppm, less than or equal to 1.5 ppm, or less than or equal to 1.25 ppm. Combinations of the above-referenced ranges are also possible (e.g., the liquid comprises dissolved palmitoylethanolamide at a concentration greater than or equal to 1 ppm and less than or equal to 20 ppm, the liquid comprises dissolved palmitoylethanolamide at a concentration greater than or equal to 10 ppm and less than or equal to 15 ppm). Other ranges are also possible.

As described above, in certain embodiments, the palmitoylethanolamide may be suspended in the liquid (e.g., aqueous solution). In certain aspects, the composition comprises suspended palmitoylethanolamide at an amount greater than or equal to 1 wt. %, greater than or equal to 2 wt. %, greater than or equal to 5 wt. %, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, greater than or equal to 40 wt. %, greater than or equal to 45 wt. %, greater than or equal to 50 wt. %, greater than or equal to 55 wt. %, greater than or equal to 60 wt. %, greater than or equal to 65 wt. %, greater than or equal to 70 wt. %, or greater than or equal to 75 wt. % versus the total weight of the composition. In some embodiments, the composition comprise suspended palmitoylethanolamide in an amount less than or equal to 80 wt. %, less than or equal to 75 wt. %, less than or equal to 70 wt. %, less than or equal to 65 wt. %, less than or equal to 60 wt. %, less than or equal to 55 wt. %, less than or equal to 50 wt. %, less than or equal to 45 wt. %, less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, less than or equal to 5 wt. %, or less than or equal to 2 wt. % versus the total weight of the composition. Combinations of the above-referenced ranges are also possible (e.g., the composition comprises suspended palmitoylethanolamide in an amount greater than or equal to 1 wt. % and less than or equal to 75 wt. % versus the total weight of the composition, the composition comprises suspended palmitoylethanolamide in an amount greater than or equal to 10 wt. % and less than or equal to 50 wt. % versus the total weight of the composition). Other ranges are also possible.

According to some embodiments, the articles and compositions described herein comprise one or more active pharmaceutical agents. The active pharmaceutical agent may be a therapeutic, diagnostic, and/or enhancement agent, including but not limited to drugs, nutrients, microorganisms, in vivo sensors, and tracers. In some embodiments, the active pharmaceutical agent, is a therapeutic, nutraceutical, prophylactic or diagnostic agent. The active pharmaceutical agent may be dissolved in the liquid (e.g., aqueous solution). For example, the active pharmaceutical agent may be a solid and/or gas dissolved in the liquid. In certain aspects, the active pharmaceutical agent is suspended in the liquid as a solid (e.g., as a powder).

In an exemplary set of embodiments, the active pharmaceutical agent comprises a cannabinoid and/or derivative(s) thereof. Non-limiting examples of cannabinoids include tetrahydrocannabinol (THC), cannabidiol (CBD), cannabigerol, tetrahydrocannabivarin, cannabidivarin, and cannabichromene.

In certain aspects, one or more active pharmaceutical agents may exhibit synergistic effects with hydrogen gas and/or palmitoylethanolamide. For example, may exhibit synergistic effects for certain applications such as for the treatment of animal and human diseases, for improvement in athletic performance, for the enhancement of the overall health of a subject, or the like. In some non-limiting embodiments, one or more active pharmaceutical agents (e.g., THC, CBD) and hydrogen gas and/or palmitoylethanolamide may synergistically provide anti-inflammatory effects to a subject. In addition, one or more active pharmaceutical agents (e.g., THC, CBD) and hydrogen gas and/or palmitoylethanolamide may synergistically relieve symptoms and/or treat a subject with arthritis and/or rheumatoid arthritis.

Active pharmaceutical agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and/or biopharmaceuticals. Certain agents, for example, may include molecules such as proteins, peptides, hormones, nucleic acids, gene constructs, and the like, for use in therapeutic, diagnostic, and/or enhancement areas, including, but not limited to medical or veterinary treatment, prevention, diagnosis, and/or mitigation of disease or illness. Non-limiting examples include HMG co-A reductase inhibitors (statins) like rosuvastatin; nonsteroidal anti-inflammatory drugs like meloxicam; selective serotonin reuptake inhibitors like escitalopram; blood thinning agents like clopidogrel; steroids like prednisone; antipsychotics like aripiprazole and risperidone; analgesics like buprenorphine, antagonists like naloxone, montelukast, and memantine; cardiac glycosides like digoxin; alpha blockers like tamsulosin; cholesterol absorption inhibitors like ezetimibe; metabolites like colchicine; antihistamines like loratadine and cetirizine; opioids like loperamide; proton-pump inhibitors like omeprazole; antibiotics like doxycycline, ciprofloxacin, and azithromycin; anti-malarial agents, and synthroid/levothyroxine; substance abuse treatment like methadone and varenicline; family planning substances like hormonal contraception; psychotropic substances like cannabinoids; performance enhancement substances like stimulants such as caffeine; and nutrition and supplements like protein, folic acid, calcium, iodine, iron, zinc, thiamine, niacin, vitamin C, vitamin D, and/or other vitamin or mineral supplements.

In certain embodiments, the active pharmaceutical agent is one or more specific therapeutic agents. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents, antihistamines, antimigraine drugs, hormones, pro staglandins, antimicrobials (including antibiotics, antifungals, antivirals, antiparasitics), antimuscarinics, anxioltyics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics an/ot anti-narcoleptics. Nutraceuticals such as vitamins, supplements such as calcium or biotin, or natural ingredients such as plant extracts or phytohormones, may also be present in the composition. In some cases, two or more active pharmaceutical agents may be present (e.g., each independently at the concentrations below). Further description of active pharmaceutical agents is described in U.S. patent application Ser. No. 15/671,465, entitled "Medication Enhancement Using Hydrogen."

The liquid may comprise one or more active pharmaceutical agents in any of a variety of suitable amounts. For example, in some embodiments, the liquid (e.g., aqueous solution) comprises an active pharmaceutical agents at a concentration greater than or equal to 1 ppm, greater than or equal to 1.25 ppm, greater than or equal to 1.5 ppm, greater than or equal to 1.75 ppm, greater than or equal to 2 ppm, greater than or equal to 2.25 ppm, greater than or equal to 2.5 ppm, greater than or equal to 2.75 ppm, greater than or equal to 3 ppm, greater than or equal to 3.25 ppm, greater than or equal to 3.5 ppm, greater than or equal to 3.75 ppm, greater than or equal to 4 ppm, greater than or equal to 4.25 ppm, greater than or equal to 4.5 ppm, greater than or equal to 4.75 ppm, greater than or equal to 5 ppm, greater than or equal to 5.5 ppm, greater than or equal to 6 ppm, greater than or equal to 6.5 ppm, greater than or equal to 7 ppm, greater than or equal to 7.5 ppm, greater than or equal to 8 ppm, greater than or equal to 8.5 ppm, greater than or equal to 9 ppm, greater than or equal to 9.5 ppm, greater than or equal to 10 ppm, greater than or equal to 11 ppm, greater than or equal to 12 ppm, greater than or equal to 13 ppm, greater than or equal to 14 ppm, greater than or equal to 15 ppm, greater than or equal to 16 ppm, greater than or equal to 17 ppm, greater than or equal to 18 ppm, or greater than or equal to 19 ppm.

In certain embodiments, the liquid (e.g., aqueous solution) comprises an active pharmaceutical agent at a concentration less than or equal to 20 ppm, less than or equal to 19 ppm, less than or equal to 18 ppm, less than or equal to 17 ppm, less than or equal to 16 ppm, less than or equal to 15 ppm, less than or equal to 14 ppm, less than or equal to 13 ppm, less than or equal to 12 ppm, less than or equal to 11 ppm, less than or equal to 10 ppm, less than or equal to 9.5 ppm, less than or equal to 9 ppm, less than or equal to 8.5 ppm, less than or equal to 8 ppm, less than or equal to 7.5 ppm, less than or equal to 7 ppm, less than or equal to 6.5 ppm, less than or equal to 5 ppm, less than or equal to 4.75 ppm, less than or equal to 4.5 ppm, less than or equal to 4.25 ppm, less than or equal to 4 ppm, less than or equal to 3.75 ppm, less than or equal to 3.5 ppm, less than or equal to 3.25 ppm, less than or equal to 3 ppm, less than or equal to 2.75 ppm, less than or equal to 2.5 ppm, less than or equal to 2.25 ppm, less than or equal to 2 ppm, less than or equal to 1.75 ppm, less than or equal to 1.5 ppm, or less than or equal to 1.25 ppm. Combinations of the above-referenced ranges are also possible (e.g., the liquid comprises an active pharmaceutical agent at a concentration greater than or equal to 1 ppm and less than or equal to 20 ppm, the liquid comprises an active pharmaceutical agent at a concentration greater than or equal to 10 ppm and less than or equal to 15 ppm). Other ranges are also possible.

Advantageously, the administration of a composition comprising hydrogen gas, palmitoylethanolamide, and/or one or more active pharmaceutical agents to a subject may result in significantly higher uptake rates (e.g., a reduction in the amount of time before the subject exhibits an effect of the active pharmaceutical agent) as compared to administration of the active pharmaceutical agent alone. In some embodiments, the composition comprising hydrogen and/or palmitoylethanolamide may advantageously permit lower concentrations of active pharmaceutical agents to be administered to a subject as compared to administration of the active pharmaceutical agent alone, while exhibiting substantially similar effects of the active pharmaceutical agent. By way of example, a subject administered a composition comprising a cannabinoid (e.g., tetrahydrocannabinol), hydrogen, and palmitoylethanolamide may exhibit a psychotropic effect(s) within minutes (e.g., less than 5 minutes) as compared to administration of the same concentration of cannabinoid alone, which may take greater than 30 minutes or more.

In certain embodiments, the article and compositions described herein comprise one or more noble gases. Without wishing to be bound by theory, while the one or more noble gases may not be directly involved in any chemical reactions, such gases may participate in physical interactions within a subject (for example, by blocking receptors, creating size exclusion effects, and/or by competing with proteins), thereby resulting in various biological effects. This may be useful, for example, for the treatment of animal and human diseases, for improvement in athletic performance, for the enhancement of the overall health of a subject, or the like.

For example, in one set of embodiments, a noble gas (e.g., xenon) may be used to induce cardioprotection and/or neuroprotection through a variety of mechanisms. In certain cases, a composition as described herein can be used to treat conditions such as ischemia (e.g., partial ischemia) or restriction in blood supply to tissues. For instance, a composition may be administered to a subject to protect neural and/or cardiac function. Without wishing to be bound by theory, it is believed that xenon may affect $Ca^{2+}$, $K^+$, KATP\HIF, and/or NMDA antagonism; xenon may also activate PKC-epsilon, p38-MAPK, ATP-sensitive potassium channel, and/or hypoxia inducible factor 1 alpha (HIF1a), thereby allowing cardioprotective and/or neuroprotective effects to occur.

In another set of embodiments, one or more noble gases (e.g., xenon) may be used to increase production of erythropoietin. This may be useful, for example, to increase red blood cells (e.g., to treat anemic subjects), or improve athletic performance. Without wishing to be bound by any theory, it is believed that xenon may enhance production of HIF1a, which is a transcription factor able to respond to hypoxic conditions. Accordingly, in some embodiments, a composition as described herein can be used to treat anemia or other conditions in a subject. In another set of embodiments, a composition as described herein may be used to increase a subject's physical energy levels (e.g., for improvement in athletic performance).

In addition, in low doses, xenon may cause certain analgesic effects, which may facilitate improved athletic performance in some cases (e.g., due to lower or reduced pain). For example, xenon may inhibit nicotinic acetylcholine alpha-4-beta-2 receptors, plasma membrane $Ca^{2+}$ ATPase, and/or the serotonin 5-HT$_3$ receptor. Xenon may also be an antagonist of high-affinity glycine-site N-methyl-D-aspartic acid (NMDA), or it may activate the two-pore domain potassium channel TREK-1.

In some cases, xenon and other and other noble gases may exhibit synergistic effects with hydrogen gas and/or palmitoylethanolamide (e.g., for certain applications such as for the treatment of animal and human diseases, for improvement in athletic performance, for the enhancement of the overall health of a subject, or the like).

In some aspects, the one or more noble gases are dissolved in the liquid (e.g., aqueous solution). The one or more noble gases may be present in the headspace of the container, as is explained herein in further detail.

Non-limiting examples of suitable noble gases that may be present in the liquid include helium, neon, argon, krypton, xenon, and/or radon. In a particular set of embodiments, the noble gas is xenon gas. In some cases, two or more noble gases may be present (e.g., each independently at the concentrations below). The noble gas may be substantially dissolved and/or suspended in the liquid. For example, the mole fraction solubility of xenon in water at 25° C. and 1 atm is generally $7.890 \times 10^{-5}$. In some embodiments, the amount of noble gas dissolved in the liquid is greater than the amount of noble gas that would be dissolved in the liquid at the mole fraction solubility of the noble gas in water determined at 25° C. and 1 atm. For example, the liquid may be under a pressure greater than 1 atm and/or a temperature greater than 25° C., (e.g., as discussed below), which may facilitate greater amounts. Further description of noble gases is described in U.S. patent application Ser. No. 15/834,262, entitled "Water and Other Liquids Containing Hydrogen and/or Noble Gases," U.S. patent application Ser. No. 15/986,885, entitled "Systems and Methods for Treatments Using Hydrogen and/or Noble Gases," and U.S. patent application Ser. No. 15/671,391, entitled, "Methods and Systems for Preparing Compositions," all of which are incorporated herein by reference in their entirety.

The noble gas may be present in the liquid in a particular amount. For example, in some embodiments, the noble gas is present in an amount of greater than or equal to 1 ppm, greater than or equal to 1.25 ppm, greater than or equal to 1.5 ppm, greater than or equal to 1.75 ppm, greater than or equal to 2 ppm, greater than or equal to 2.25 ppm, greater than or equal to 2.5 ppm, greater than or equal to 2.75 ppm, greater than or equal to 3 ppm, greater than or equal to 3.25 ppm, greater than or equal to 3.5 ppm, greater than or equal to 3.75 ppm, greater than or equal to 4 ppm, greater than or equal to 4.25 ppm, greater than or equal to 4.5 ppm, greater than or equal to 4.75 ppm, greater than or equal to 5 ppm, greater than or equal to 5.5 ppm, greater than or equal to 6 ppm, greater than or equal to 6.5 ppm, greater than or equal to 7 ppm, greater than or equal to 7.5 ppm, greater than or equal to 8 ppm, greater than or equal to 8.5 ppm, greater than or equal to 9 ppm, greater than or equal to 9.5 ppm, greater than or equal to 10 ppm, greater than or equal to 11 ppm, greater than or equal to 12 ppm, greater than or equal to 13 ppm, greater than or equal to 14 ppm, greater than or equal to 15 ppm, greater than or equal to 16 ppm, greater than or equal to 17 ppm, greater than or equal to 18 ppm, or greater than or equal to 19 ppm.

In certain embodiments, the noble gas is present in the liquid in an amount of less than or equal to 20 ppm, less than or equal to 19 ppm, less than or equal to 18 ppm, less than or equal to 17 ppm, less than or equal to 16 ppm, less than or equal to 15 ppm, less than or equal to 14 ppm, less than or equal to 13 ppm, less than or equal to 12 ppm, less than or equal to 11 ppm, less than or equal to 10 ppm, less than or equal to 9.5 ppm, less than or equal to 9 ppm, less than or equal to 8.5 ppm, less than or equal to 8 ppm, less than or equal to 7.5 ppm, less than or equal to 7 ppm, less than or equal to 6.5 ppm, less than or equal to 5 ppm, less than or equal to 4.75 ppm, less than or equal to 4.5 ppm, less than or equal to 4.25 ppm, less than or equal to 4 ppm, less than or equal to 3.75 ppm, less than or equal to 3.5 ppm, less than or equal to 3.25 ppm, less than or equal to 3 ppm, less than or equal to 2.75 ppm, less than or equal to 2.5 ppm, less than or equal to 2.25 ppm, less than or equal to 2 ppm, less than or equal to 1.75 ppm, less than or equal to 1.5 ppm, or less than or equal to 1.25 ppm. Combinations of the above-referenced ranges are also possible (e.g., greater than or equal to 1 ppm and less than or equal to 20 ppm, greater than or equal to 10 ppm and less than or equal to 15 ppm). Other ranges are also possible. The noble gas may include xenon, and/or other gases as discussed herein.

In some embodiments, the liquid may comprise one or more additives. Non-limiting examples of additives include sugar, electrolytes, caffeine, salt, flavoring, vitamins, herbs, amino acids, tea extracts, seed extracts, fruit extracts, and combinations thereof.

The liquid may comprise the one or more additives in any of a variety of suitable amounts. For example, in some embodiments, the liquid (e.g., aqueous solution) comprises the additive in an amount greater than or equal to 1 wt. %, greater than or equal to 2 wt. %, greater than or equal to 5 wt. %, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, greater than or equal to 40 wt. %, greater than or equal to 45 wt. %, greater than or equal to 50 wt. %, or greater than or equal to 55 wt. % versus the total weight of the composition. In certain embodiments, the liquid (e.g., aqueous solution) comprises the additive in an amount less than or equal to 60 wt. %, less than or equal to 55 wt. %, less than or equal to 50 wt. %, less than or equal to 45 wt. %, less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, less than or equal to 5 wt. %, or less than or equal to 2 wt. % versus the total weight of the composition. Combinations of the above-referenced ranges are also possible (e.g., the liquid comprises the additive in an amount greater than or equal to 1 wt. % and less than or equal to 55 wt. %, the liquid comprises the additive in an amount greater than or equal to 10 wt. % and less than or equal to 30 wt. %). Other ranges are also possible.

In some embodiments, the composition comprises hydrogen, palmitoylethanolamide, one or more active pharmaceutical agents, and/or one or more noble gases in the ranges listed herein with the remainder of the composition being excipient.

The composition may comprise any of a variety of suitable amounts of excipient. In certain embodiments, for example, the composition comprises an excipient in an amount greater than or equal to 1 wt. %, greater than or equal to 2 wt. %, greater than or equal to 5 wt. %, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, greater than or equal to 40 wt. %, greater than or equal to 45 wt. %, greater than or equal to 50 wt. %, greater than or equal to 55 wt. %, greater than or equal to 60 wt. %, greater than or equal to 65 wt. %, greater than or equal to 70 wt. %, or greater than or equal to 75 wt. % versus the total weight of the composition. In some embodiments, the composition comprise an excipient in an amount less than or equal to 80 wt. %, less than or equal to 75 wt. %, less than or equal to 70 wt. %, less than or equal to 65 wt. %, less than or equal to 60 wt. %, less than or equal to 55 wt. %, less than or equal to 50 wt. %, less than or equal to 45 wt. %, less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, less than or equal to 5 wt. %, or less than or equal to 2 wt. % versus the total weight of the composition. Combinations of the above-referenced ranges are also possible (e.g., the composition comprises an excipient in an amount greater than or equal to 1 wt. % and less than or equal to 75 wt. % versus the total weight of the composition, the composition comprises an excipient in an amount greater than or equal to 10 wt. % and less than or equal to 50 wt. % versus the total weight of the composition). Other ranges are also possible.

In some cases, the liquid (e.g., aqueous solution) may be contained within a container. Referring to the FIGURE, article 100 may comprise liquid (e.g., aqueous solution) 110 contained within container 120. In certain embodiments, the container may be sealed (e.g., to the external atmosphere). For example, in certain embodiments, the container may be sealed such that the liquid and/or gases (e.g., hydrogen gas, one or more noble gases) within the container are not able to substantially exit the container. In some cases, the seal may be removable, such that the liquid may be removed from the container and/or orally administered to a subject. For example, in an exemplary embodiment, the container is a can and the can may be unsealed by breaking the seal of the can (e.g., via a pull-tab, push-tab, or stay-tab associated with the seal). In another exemplary embodiment, the container is a bottle or pouch, and the container may be unsealed by removing a cap associated with an opening of the container. Upon unsealing the container, the liquid may be ingested (e.g., drunk) by the subject.

Non-limiting examples of suitable types of containers include cans (e.g., aluminum or tin cans), bottles, jars, pouches, boxes, and bags. In certain embodiments, the container may be a pill or a capsule (e.g., gel-capsule). Other containers are also possible and those of ordinary skill in the art would be capable of selecting suitable containers based upon the teachings of this specification.

The container may comprise any of a variety of suitable materials. For example, in some embodiments, the container may comprise a material such as metal (e.g., aluminum, tin, iron), metal alloys (e.g., steel), polymer (e.g., polyethylene, polystyrene, polypropylene, polyether ether ketones, polyethylene terephthalate, polyvinylchloride), glass (e.g., borosilicate glass), resin, and combinations thereof. In some cases, the container is able to contain an elevated pressure therein (e.g., a pressure greater than atmospheric pressure).

In addition, in some embodiments, one or more coatings or other materials may be used in conjunction with the container to facilitate retention of gases within the container. In certain aspects, the one or more coatings or materials may be relatively gas-impermeable. A variety of gas-impermeable materials may be readily obtained commercially, and coated onto a surface of the container and/or embedded within the materials forming the container. Non-limiting examples of gas-impermeable materials include polyester, nylon (e.g., MXD6 nylon or nylon 6), ethylene vinyl alcohol (EVA), silicon oxides ($SiO_x$), or the like. Further description of suitable containers and container coatings for containing compositions are described in U.S. patent application Ser. No. 15/835,602, entitled "Barriers for Glass and Other Materials," and U.S. patent application Ser. No. 15/671,403, entitled "Barriers to Hydrogen and Other Materials," both of which are incorporated herein by reference in their entirety.

In some embodiments, the liquid (e.g., aqueous solution) is contained within a container at a particular pressure. In certain aspects, the pressure is greater than atmospheric pressure. The pressure may be created within the container using any of a variety of gases, including air, nitrogen, carbon dioxide, water vapor, hydrogen gas, or the like, as well as combinations of these and/or other suitable gases. Such gases may be at equilibrium with the liquid within the container. In addition, in some cases, one or more of the gases may be present in an amount such that at equilibrium, those gases are dissolved within the liquid at saturation concentrations.

For example, in certain embodiments, the container contains a pressure greater than or equal to 1 psi (1 psi is about 6894.757 Pa), greater than or equal to 2 psi, greater than or equal to 3 psi, greater than or equal to 5 psi, greater than or equal to 7 psi, greater than or equal to 10 psi, greater than or equal to 12 psi, greater than or equal to 15 psi, greater than or equal to 18 psi, greater than or equal to 20 psi, greater than or equal to 25 psi, greater than or equal to 30 psi, greater than or equal to 35 psi, greater than or equal to 40 psi, or greater than or equal to 45 psi greater than atmospheric pressure. In some embodiments, the container contains a pressure less than or equal to 50 psi, less than or equal to 45 psi, less than or equal to 40 psi, less than or equal to 35 psi, less than or equal to 30 psi, less than or equal to 25 psi, less than or equal to 20 psi, less than or equal to 18 psi, less than or equal to 15 psi, less than or equal to 12 psi, less than or equal to 10 psi, less than or equal to 7 psi, less than or equal to 5 psi, less than or equal to 3 psi, or less than or equal to 2 psi greater than atmospheric pressure. Combinations of the above-referenced ranges are also possible (e.g., the container contains a pressure greater than or equal to 1 psi and less than or equal to 50 psi greater than atmospheric pressure, the container contains a pressure greater than or equal to 10 psi and less than or equal to 20 psi greater than atmospheric pressure). Other ranges are also possible.

In some embodiments, the container comprises a gaseous headspace. For example, referring to the FIGURE, in some cases, article 100 comprises gaseous headspace 115. The article may comprise any suitable amount of gaseous headspace within the container. In some embodiments, the gaseous headspace occupies greater than or equal to 0.1 percent volume (vol. %), greater than or equal to 0.2 vol. %, greater than or equal to 0.25 vol. %, greater than or equal to 0.5 vol. %, greater than or equal to 0.75 vol. %, greater than or equal to 1 vol. %, greater than or equal to 1.25 vol. %, greater than or equal to 1.5 vol. %, greater than or equal to 1.75 vol. %, greater than or equal to 2 vol. %, greater than or equal to 2.25 vol. %, greater than or equal to 2.5 vol. %, greater than or equal to 3 vol. %, greater than or equal to 3.5 vol. %, greater than or equal to 4 vol. %, or greater than or equal to 4.5 vol. % of the volume contained by the container. In certain embodiments, the headspace occupies less than or equal to 5 vol. %, less than or equal to 4.5 vol. %, less than or equal to 4 vol. %, less than or equal to 3.5 vol. %, less than or equal to 3 vol. %, less than or equal to 2.5 vol. %, less than or equal to 2.25 vol. %, less than or equal to 2 vol. %, less than or equal to 1.75 vol. %, less than or equal to 1.5 vol. %, less than or equal to 1.25 vol. %, less than or equal to 1 vol. %, less than or equal to 0.75 vol. %, less than or equal to 0.5 vol. %, less than or equal to 0.25 vol. %, or less than or equal to 0.2 vol. % of the volume contained by the container. Combinations of the above-referenced ranges are also possible (e.g., greater than or equal to 0.1 vol. % and less than or equal to 5 vol. %). Other ranges are also possible.

In some embodiments, the gaseous headspace comprises hydrogen gas. For example, referring to the FIGURE, gaseous headspace 115 may comprise hydrogen gas 200b. As discussed herein, other gases may be present in the headspace as well (e.g., one or more noble gases may be present at the percent volumes listed below). In some embodiments, when hydrogen gas is present in the headspace, the concentration of hydrogen gas is greater than the concentration of hydrogen gas that would result from the saturation vapor pressure of hydrogen gas in the liquid (e.g., aqueous solution).

In certain aspects, the headspace comprises greater than or equal to 0.00001 vol. %, greater than or equal to 0.00005 vol. %, greater than or equal to 0.0001 vol. %, greater than or equal to 0.0005 vol. %, greater than or equal to 0.001 vol. %, greater than or equal to 0.005 vol. %, greater than or equal to 0.01 vol. %, greater than or equal to 0.05 vol. %, greater than or equal to 0.1 vol. %, greater than or equal to 0.5 vol. %, greater than or equal to 1 vol. %, greater than or equal to 2 vol. %, greater than or equal to 5 vol. %, greater than or equal to 10 vol. %, greater than or equal to 20 vol. %, greater than or equal to 30 vol. %, greater than or equal to 40 vol. %, greater than or equal to 50 vol. %, or greater than or equal to 60 vol. % hydrogen gas versus the total volume of the headspace. In certain embodiments, the headspace comprises less than or equal to 70 vol. %, less than or equal to 60 vol. %, less than or equal to 50 vol. %, less than or equal to 40 vol. %, less than or equal to 30 vol. %, less than or equal to 20 vol. %, less than or equal to 10 vol. %, less than or equal to 5 vol. %, less than or equal to 2 vol. %, less than or equal to 1 vol. %, less than or equal to 0.5 vol. %, less than or equal to 0.1 vol. %, less than or equal to 0.05 vol. %, less than or equal to 0.01 vol. %, less than or equal to 0.005 vol. %, less than or equal to 0.001 vol. %, less than or equal to 0.0005 vol. %, less than or equal to 0.0001 vol. %, or less than or equal to 0.00005 vol. % hydrogen gas versus the total volume of the headspace. Combinations of the above-referenced ranges are also possible (e.g., the headspace comprises greater than or equal to 0.00001 vol. % and less than or equal to 10 vol. % hydrogen gas versus the total volume of the headspace, the headspace comprises greater than or equal to 0.01 vol. % and less than or equal to 1 vol. % versus the total volume of the headspace). Other ranges are also possible.

As mentioned, the liquid may be any of a variety of drinkable liquids in various embodiments, such as water, a fruit juice, a juice-like beverage (e.g., powdered drinks such as Crystal Light®, Kool-Aid®, or the like) coffee, tea, a sports drink, an energy drink, soda pop, milk (e.g., cow's milk, goat's milk, sheep's milk, low-fat milk, whole milk, cream, chocolate milk), an alcoholic drink (e.g., mixed alcoholic beverages, wine, beer), and the like. In some cases, the composition may be in the form of an intravenous fluid (e.g., saline, Ringer's lactate).

In some embodiments, the liquid comprises hydrogen gas and/or palmitoylethanolamide, in the ranges listed above, with the remainder of the liquid being water. In certain embodiments, the liquid (e.g., aqueous solution) comprises greater than or equal to 90 wt. %, greater than or equal to 91 wt. %, greater than or equal to 92 wt. %, greater than or equal to 93 wt. %, greater than or equal to 94 wt. %, greater than or equal to 95 wt. %, greater than or equal to 96 wt. %, greater than or equal to 97 wt. %, greater than or equal to 98 wt. %, greater than or equal to 99 wt. %, greater than or equal to 99.5 wt. %, or greater than or equal to 99.9 wt. % water versus the total weight of the liquid (e.g., aqueous solution). In some embodiments, the liquid (e.g., aqueous solution) comprises less than or equal to 99.99 wt. %, less than or equal to 99.9 wt. %, less than or equal to 99.5 wt. %, less than or equal to 99 wt. %, less than or equal to 98 wt. %, less than or equal to 97 wt. %, less than or equal to 96 wt. %, less than or equal to 95 wt. %, less than or equal to 94 wt. %, less than or equal to 93 wt. %, less than or equal to 92 wt. %, or less than or equal to 91 wt. % water versus the total weight of the liquid (e.g., aqueous solution). Combinations of the above-referenced ranges are also possible (e.g., the liquid comprises greater than or equal to 90 wt. % and less than or equal to 99.99 wt. % water versus the total weight of the liquid, the liquid comprises greater than or equal to 95 wt. % and less than or equal to 99.99 wt. % water versus the total weight of the liquid). Other ranges are also possible.

In some embodiments, the liquid (e.g., aqueous solution) contained within the container fills greater than or equal to 50 vol. %, greater than or equal to 75 vol. %, greater than or equal to 80 vol. %, greater than or equal to 85 vol. %, greater than or equal to 90 vol. %, greater than or equal to 92 vol. %, greater than or equal to 95 vol. %, greater than or equal to 98 vol. %, greater than or equal to 99 vol. %, greater than or equal to 99.5 vol. %, or greater than or equal to 99.9 vol. % of the volume of the sealed container. In some aspects, the liquid (e.g., aqueous solution) contained within the container fills less than or equal to 99.99 vol. %, less than or equal to 99.9 vol. %, less than or equal to 99.5 vol. %, less than or equal to 99 vol. %, less than or equal to 98 vol. %, less than or equal to 95 vol. %, less than or equal to 92 vol. %, less than or equal to 90 vol. %, less than or equal to 85 vol. %, less than or equal to 80 vol. %, or less than or equal to 75 vol. % of the volume of the sealed container. Combinations of the above-referenced ranges are also possible (e.g., the liquid contained within the container fills greater than or equal to 50 vol. % and less than or equal to 99.99 vol. % of the volume of the sealed container, the liquid contained with the container fills greater than or equal to 75 vol. % and less than or equal to 90 vol. % of the volume of the sealed container).

In some embodiments, the articles (e.g., sealed containers) described herein are configured to have a relatively long shelf life with respect to the gases contained therein. In certain embodiments, the hydrogen gas does not substantially leak from the sealed container for at least 7 days, or longer (e.g., 14 days, 28 days, 56 days, etc.). For example, in some embodiments, greater than or equal to 50 vol. %, greater than or equal to 75 vol. %, greater than or equal to 80 vol. %, greater than or equal to 85 vol. %, greater than or equal to 90 vol. %, greater than or equal to 92 vol. %, greater than or equal to 95 vol. %, greater than or equal to 98 vol. %, greater than or equal to 99 vol. %, greater than or equal to 99.5 vol. %, or greater than or equal to 99.9 vol. % of the hydrogen gas is present in the sealed container and/or in the headspace 7 days after sealing the container. In certain embodiments, less than or equal to 99.99 vol. %, less than or equal to 99.9 vol. %, less than or equal to 99.5 vol. %, less than or equal to 99 vol. %, less than or equal to 98 vol. %, less than or equal to 95 vol. %, less than or equal to 92 vol. %, less than or equal to 90 vol. %, less than or equal to 85 vol. %, less than or equal to 80 vol. %, or less than or equal to 75 vol. % of the hydrogen gas is present in the sealed container and/or in the headspace 7 days after sealing the container. Combinations of the above-referenced ranges are also possible (e.g., greater than or equal to 50 vol. % and less than or equal to 99.99 vol. % of the hydrogen gas is present in the sealed container and/or in the headspace 7 days after sealing the container, greater than or equal to 75 vol. % and less than or equal to 90 vol. % of the hydrogen gas is present in the sealed container and/or in the headspace 7 days after sealing the container). Other ranges are also possible.

In some embodiments, the composition may be used to increase the energy levels and/or overall feeling or well-being of a subject. For example, the composition may reduce oxidative stress and/or reduce muscle fatigue (e.g., after exercise and/or athletic activity). In certain embodiments, the composition may improve a subject's overall well-being including, for example, a feeling of increased energy levels, hastened recovery after exercise, improved memory, increased strength, and/or reduced tiredness. In some cases, the composition may be particularly delectable to the subject. In some embodiments, the composition may provide performance enhancement to a subject while, for example, exercising and/or performing athletic activities. In addition, in some cases, the composition may be used to treat a disease, disorder, or other clinically recognized condition, or for prophylactic purposes, or for providing physiological benefits, and has a clinically significant effect on the body of the subject to treat and/or prevent the disease, disorder, or condition, and/or has a clinically significant effect on the subject's physiology.

In some embodiments, the composition comprising hydrogen and palmitoylethanolamide is an ingestible composition. One of ordinary skill in the art would understand that the term "ingestible" as used herein is not intended to encompass any and all substances and/or compositions that may be placed in a subject's body (e.g., via swallowing or drinking). Ingestible compositions are those that are edible (e.g., typically intended to be digested and absorbed by the body of the subject for nourishment, pleasure, therapeutic effect, and/or energy). In some embodiments, the ingestible composition is non-toxic, although those of ordinary skill in the art would understand that some ingestible compositions, such as therapeutic agents, may have some negligible level of toxicity but which provide a therapeutic benefit. By way of example, a stainless steel ball, while a capable of being swallowed by a subject, would not be considered an ingestible composition (e.g., as it provides no nourishing, pleasure, or therapeutic effect on the subject). Similarly, antifreeze, while a liquid, would not be considered an ingestible composition (e.g., as it provides a detrimental effect on the body of the subject). By contrast, and by way of example without wishing to be limited by such, a liquid such as water or food such as pudding, which are generally consumed for nourishment and/or pleasure, would each be considered an ingestible composition.

In certain embodiments, the ingestible liquid (e.g., aqueous solution) may be administered to a subject (e.g., drunk by a subject). For example, the article comprising the liquid may be administered orally, intravenously, rectally, nasally (e.g., via a nasal spray, via a nasal dropper), or uretherally (e.g., via a catheter). In addition, in some embodiments, the solution may be self-administered by the subject. In certain embodiments, the composition may be administered to a subject via injection (e.g., via syringe, needle, or the like). In one set of embodiments, a composition as described herein is used to treat a subject (e.g., a human subject). To "treat" a condition means to reduce or eliminate a sign or symptom of the condition, to stabilize the condition, and/or to reduce or slow further progression of the condition. In some cases, the subject may be one that has or is at risk for a disorder or condition. The condition may be, for example, a disease, such as discussed herein.

In some embodiments, the composition may be configured to be administered to a subject topically (e.g., a topical composition). Non-limiting examples of topical compositions include topical solutions, cosmetics, creams (e.g., steroidal creams, antibiotic creams), foams, pastes (e.g., toothpastes), gels, lotions, soaps, jellies (e.g., petroleum jelly), lip balms, shampoos, and ointments.

In some cases, the composition may be configured to be administered to a subject as a food. For example, the composition may include a food such as frozen foods including but not limited to, for example, ice cream, sorbet, gelato, or the like. In some cases, the composition may include a food such as an ingestible colloid, gel, and/or suspension including but not limited to, for example, puddings, custards, and Jell-O®. In an illustrative embodiment, hydrogen gas and/or palmitoylethanolamide may be added to a composition such as a food which does not require further heating prior to ingestion (e.g., refrigerated prepared foods, liquids, colloids, gels, and/or suspensions) such that, for example, the hydrogen gas and/or palmitoylethanolamide are not boiled out of the composition.

In certain embodiments, a method comprises administering (e.g., orally administering) the liquid (e.g., aqueous solution) to a subject. In some aspects, for example, a method comprises drinking the liquid (e.g., aqueous solution). In certain embodiments, a method comprises swallowing the liquid (e.g., aqueous solution), which may optionally be encapsulated in a pill and/or a capsule, such as a gel-capsule. Alternatively, a method may comprise intravenously administering the liquid (e.g., aqueous solution) to a subject. In some embodiments, the liquid (e.g., aqueous solution) comprises hydrogen gas at a concentration greater than or equal to 1 ppm, and dissolved and/or suspended palmitoylethanolamide (e.g., at a concentration greater than or equal to 1 ppm and less than or equal to 20 ppm).

In one set of embodiments, the composition, prior to administration to a subject, may be contained within a sealed container (e.g., as described herein). For example, the aqueous solution may be contained within a can, bottle, jar, pouch, box, bag, or capsule. In some cases, the container may be unsealed just before administration to a subject. For example, the container may be unsealed and then administered to a subject (including self-administration) within 1 hour of unsealing the container, or within 45 minutes, within 30 minutes, within 20 minutes, within 15 minutes, within 10 minutes, within 5 minutes, within 4 minutes, within 3 minutes, within 2 minutes, or within 1 minute of unsealing.

When the composition is administered to a subject, effective amounts will depend on the particular condition being treated and the desired outcome. A therapeutically effective dose may be determined by those of ordinary skill in the art, for instance, employing factors such as those described herein and using no more than routine experimentation.

In administering the composition to a subject, dosing amounts, dosing schedules, routes of administration, and the like may be selected so as to affect known activities of these compositions. Dosages may be estimated based on the results of experimental models, optionally in combination with the results of assays of compositions. Dosage may be adjusted appropriately to achieve desired drug levels, local or systemic, depending upon the mode of administration. The doses may be given in one or several administrations per day. Multiple doses per day are also contemplated in some cases to achieve appropriate systemic levels of the composition within the subject or within the active site of the subject.

The dosage may be given in some cases at the maximum amount while avoiding or minimizing any potentially detrimental side effects within the subject. The dosage of the composition that is actually administered is dependent upon factors such as the final concentration desired at the active site, the method of administration to the subject, the efficacy of the composition, the longevity of the composition within the subject, the timing of administration, the effect of concurrent treatments, etc. The dose delivered may also depend on conditions associated with the subject, and can vary from subject to subject in some cases. For example, the age, sex, weight, size, environment, physical conditions, or current state of health of the subject may also influence the dose required and/or the concentration of the composition. Variations in dosing may occur between different individuals or even within the same individual on different days. It may be preferred that a maximum dose be used, that is, the highest safe dose according to sound medical judgment. Preferably, the dosage form is such that it does not substantially deleteriously affect the subject.

Administration of the composition can be alone, or in combination with other therapeutic agents and/or compositions. In certain embodiments, a composition can be combined with a suitable pharmaceutically acceptable carrier, for example, within a suitable liquid. In general, pharmaceutically acceptable carriers suitable for use herein are well-known to those of ordinary skill in the art. As used herein, a "pharmaceutically acceptable carrier" refers to a non-toxic material that does not significantly interfere with the effectiveness of the biological activity of the active composition(s) to be administered, but is used as a formulation ingredient, for example, to stabilize or protect the active composition(s) within the composition before use. The carrier may include one or more compatible solid or liquid fillers, diluents or encapsulating substances which are suitable for administration to a human or other vertebrate animal. The term "carrier" denotes an organic or inorganic ingredient, which may be natural or synthetic, with which one or more compositions are combined to facilitate the application of the composition. The carrier may be co-mingled or otherwise mixed with one or more compositions of the present invention, and with each other, in a manner such that there is no interaction which would substantially impair the desired pharmaceutical efficacy. Those skilled in the art will know of suitable carriers, such as saline, or will be able to ascertain such, using only routine experimentation.

The formulations are administered in pharmaceutically acceptable solutions, which may routinely contain pharmaceutically acceptable concentrations of salt, buffering agents, preservatives, compatible carriers, adjuvants, emulsifiers, diluents, excipients, chelating agents, fillers, drying agents, antioxidants, antimicrobials, preservatives, binding agents, bulking agents, silicas, solubilizers, stabilizers and optionally other therapeutic ingredients, that may be used with the active composition. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, *arachis* oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions without resort to undue experimentation.

Any of the above-mentioned compositions may be provided in a kit, optionally including instructions for use of the composition for the treatment of a condition discussed herein. That is, the kit can include a description of use of the composition for participation in any biological or chemical mechanism disclosed herein associated with a condition discussed herein. The kit can include a description of use of the compositions as discussed herein. The kit also can include instructions for use of a combination of two or more compositions as described herein, or instruction for use of a combination of a composition as described herein and one or more other compositions. Instructions also may be provided for administering the composition by any suitable technique as previously described, for example, orally, intravenously, pump or implantable delivery device, or via another known route of drug delivery.

The kits described herein may also contain one or more containers, which may contain the composition and other ingredients as previously described. The kits also may contain instructions for mixing, diluting, and/or administrating the compositions in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions. In embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

In certain embodiments, the articles, compositions, and liquids (e.g., aqueous solutions) described herein are substantially non-toxic. The term "non-toxic" refers to a substance that does not comprise a toxic compound. The term "toxic" refers to a substance showing detrimental, deleterious, harmful, or otherwise negative effects on a subject, tissue, or cell when or after administering the substance to the subject or contacting the tissue or cell with the substance, compared to the subject, tissue, or cell prior to administering the substance to the subject or contacting the tissue or cell with the substance. In certain embodiments, the effect is death or destruction of the subject, tissue, or cell. In certain embodiments, the effect is a detrimental effect on the metabolism of the subject, tissue, or cell. In certain embodiments, a toxic substance is a substance that has a median lethal dose (LD50) of not more than 500 milligrams per kilogram of body weight when administered orally to an albino rat weighing between 200 and 300 grams, inclusive. In certain embodiments, a toxic substance is a substance that has an LD50 of not more than 1,000 milligrams per kilogram of body weight when administered by continuous contact for 24 hours (or less if death occurs within 24 hours) with the bare skin of an albino rabbit weighing between two and three kilograms, inclusive. In certain embodiments, a toxic substance is a substance that has an LC50 in air of not more than 2,000 parts per million by volume of gas or vapor, or not more than 20 milligrams per liter of mist, fume, or dust, when administered by continuous inhalation for one hour (or less if death occurs within one hour) to an albino rat weighing between 200 and 300 grams, inclusive.

According to some embodiments, a method of preparing a composition is described. In some aspects, the method comprises providing a container comprising a liquid (e.g., water). The method may comprise dissolving hydrogen in the water, such that the liquid (e.g., water) comprises hydrogen gas as a concentration greater than or equal to 1 ppm. Methods of dissolving hydrogen in the water are explained herein in greater detail.

The method may further comprise dissolving palmitoylethanolamide in the liquid (e.g., water), wherein the palmitoylethanolamide is dissolved in the liquid using an emulsifier. Alternatively, or in addition to dissolving the palmitoylethanolamide in the liquid, the method may comprise suspending the palmitoylethanolamide in the liquid (e.g., water), wherein the palmitoylethanolamide is suspended in the liquid using micronization. Method of micronization are described herein, including milling (e.g., ball milling), grinding, bashing, and/or pulverizing. In certain embodiments, supercritical fluids may be used in the micronization process, using, for example, supercritical antisolvents to precipitate micronized particles from solution.

Certain embodiments are related to introducing hydrogen (e.g., liquid hydrogen) and/or one or more liquid noble gases into a composition and/or a contained comprising a composition, and optionally sealing the container. In one set of embodiments, for example, the system comprises one, two, or more storage containers for storing and/or transferring liquid hydrogen and/or one or more liquid noble gases (e.g., at cryogenic temperatures). The liquid hydrogen and/or one or more liquid noble gases may be kept liquid by storing them at relatively cold temperatures (e.g., at temperatures below their respective boiling points). The storage container may be unpressurized (e.g., at atmospheric pressure, 1 atm), or may have a pressure than is greater or less than atmospheric pressure.

One or more of the storage containers (e.g., sources of liquid hydrogen and/or one or more liquid noble gases) may be in fluidic communication with a valve, optionally via one or more conduits (e.g., pipes). In some embodiments, the valve may comprise one or more materials suitable for controlling the flow of relatively cold liquids (e.g., a cryogenic liquid). In an exemplary embodiment, the valve comprises austenitic stainless steel, steel alloys, carbon steel, polytetrafluoroethylene, or combinations thereof. The valve may be, for example, a globe valve, a gate valve, a check valve, a butterfly valve, a cryogenic ball valve, or combinations thereof. Such valves and/or other components, in some cases, may be designed to flow and/or dispense particularly cold liquids (e.g., liquid hydrogen) such that the liquid does not substantially change phase (e.g., until exiting, for example, into an article, such as a container). The valve may disperse the cryogenic liquids into the article (e.g., container), and in some cases, in a relatively controlled dose (e.g., such that the amount of liquid that flows into each container is substantially the same). For example, 80%, 85%, 90%, or 95% of the containers may contain between 80% and 120%, between 85% and 115%, between 90% and 110%, or between 95% and 105% of the average amount of liquid deposited into the containers. In certain embodiments, a pressure gauge may be employed in order to gauge the amount of liquid hydrogen and/or one or more liquid noble gases from the storage containers.

In certain embodiments, after transferring the liquid hydrogen and/or one or more liquid noble gases from the storage container to the article (e.g., container), the liquid hydrogen changes phase into a gaseous phase, such that the contents (e.g., the composition, hydrogen gas, one or more liquid noble gases, and/or any additives) contained within the sealed container are pressurized (e.g., as the liquid hydrogen becomes gaseous and/or warms to a temperature greater than its respective boiling points). Advantageously, such containers described herein may provide liquids containing hydrogen gas and one or more noble gases that are shelf-stable (e.g., maintain a relatively stable concentration of hydrogen gas and/or one or more noble gases) for relatively long periods of time (e.g., at least 7 days). In some cases, such gases may be at equilibrium with being dissolved in the liquid phase. Further description of storage systems and transferring liquid hydrogen and/or liquid noble gases to liquids is described in U.S. patent application Ser. No. 15/671,465, entitled "Medication Enhancement Using Hydrogen."

A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Certain embodiments are generally directed toward use with humans. In some embodiments, a subject may demonstrate health benefits, e.g., upon drinking the liquid, or otherwise being orally administered the composition described herein.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

EXAMPLES

The following examples illustrate embodiments of certain aspects. It should be understood that the methods and/or materials described herein may be modified and/or scaled, as known to those of ordinary skill in the art.

Prophetic Example 1

A composition comprising hydrogen has and dissolved palmitoylethanolamide is provided. A container comprising water is provided. Using an emulsifier, palmitoylethanolamide is dissolved in the water such that greater than or equal to 1 mg and less than or equal to 3 mg of palmitoylethanolamide is introduced to one liter of water. A system comprising a valve configured and designed for the flow of liquid hydrogen is placed into fluidic communication with the container comprising water. Liquid hydrogen is flowed through the system such that greater than or equal to 0.1 mg and less than or equal to 5 mg of liquid hydrogen is introduced to one liter of the water.

Prophetic Example 2

A composition comprising hydrogen has and dissolved palmitoylethanolamide is provided. A container comprising water is provided. Palmitoylethanolamide is micronized to an average particle size of 500 micrometers, then added to the container comprising water such that greater than or equal to 5 mg and less than or equal to 10 mg of palmitoylethanolamide is introduced to one liter of water. A system comprising a valve configured and designed for the flow of liquid hydrogen is placed into fluidic communication with the container comprising water. Liquid hydrogen is flowed through the system such that greater than or equal to 0.1 mg and less than or equal to 5 mg of liquid hydrogen is introduced to one liter of the water.

Prophetic Example 3

A sealed container comprising a composition such as described herein is provided to a subject, such as a human subject. The composition comprises a liquid such as water (or another suitable drink), dissolved hydrogen, dissolved palmitoylethanolamide, suspended palmitoylethanolamide, and a dissolved active pharmaceutical agent (e.g., THC). The subject opens the container and promptly (e.g., within one minute) ingests (e.g., drinks) the composition. After ingestion by the subject, the effects of the hydrogen gas, palmitoylethanolamide, and THC are felt by the subject surprisingly rapidly (e.g., in less than 5 minutes), as compared to other methods which typically take tens of minutes.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
   an aqueous solution contained within a container; wherein the aqueous solution comprises palmitoylethanolamide and dissolved hydrogen gas at a concentration greater than 1 ppm, and the container contains a pressure at least 1 psi greater than atmospheric pressure.
2. The article of claim 1, wherein at least some of the palmitoylethanolamide is dissolved in the aqueous solution.
3. The article of claim 1, wherein at least some of the palmitoylethanolamide is suspended in the aqueous solution.
4. The article of claim 1, wherein the container is a can, bottle, jar, pouch, box, or bag.
5. The article of claim 1, wherein the container is sealed.
6. The article of claim 1, wherein the container further comprises a gaseous headspace.
7. The article of claim 6, wherein the gaseous headspace comprises at least 0.00001 vol. % hydrogen gas versus the total volume of the gaseous headspace.
8. The article of claim 1, wherein the aqueous solution comprises greater than or equal to 90 wt. % water versus the total weight of the aqueous solution.
9. The article of claim 1, wherein the aqueous solution is non-toxic.
10. The article of claim 1, wherein the aqueous solution comprises one or more dissolved active pharmaceutical agents.
11. The article of claim 10, wherein the one or more dissolved active pharmaceutical agents comprises a cannabinoid and/or derivatives thereof.
12. The article of claim 10, wherein the one or more dissolved active pharmaceutical agents comprises tetrahydrocannabinol.
13. The article of claim 1, wherein the aqueous solution comprises dissolved palmitoylethanolamide at a concentration greater than 1 ppm and/or suspended palmitoylethanolamide at an amount greater than 1 wt. % versus the total weight of the aqueous solution.
14. The article of claim 1, wherein the suspended palmitoylethanolamide is micronized.
15. The article of claim 14, wherein the suspended palmitoylethanolamide is micronized such that the suspended palmitoylethanolamide comprises a plurality of particles having an average particle size of less than or equal to 1 micrometer.
16. A method of treating a condition, comprising:
    providing the container of claim 1, and drinking the aqueous solution contained within the container.
17. A method of preparing a composition, comprising:
    providing a container comprising water;
    dissolving hydrogen in the water, such that the water comprises hydrogen gas at a concentration greater than or equal to 1 ppm;
    dissolving and/or suspending palmitoylethanolamide in the water, wherein palmitoylethanolamide is dissolved in the water using an emulsifier and/or suspended in the water using micronization; and
    sealing the container under a pressure at least 1 psi greater than atmospheric pressure.

* * * * *